United States Patent [19]
Roberts

[11] Patent Number: 6,166,813
[45] Date of Patent: Dec. 26, 2000

[54] RETROREFLECTOMETER AND METHOD FOR MEASURING RETROREFLECTIVITY OF MATERIALS

[75] Inventor: David Wayne Roberts, Atlanta, Ga.

[73] Assignee: Georgia Tech Research Corporation, Atlanta, Ga.

[21] Appl. No.: 09/061,732

[22] Filed: Apr. 16, 1998

Related U.S. Application Data

[60] Provisional application No. 60/044,740, Apr. 18, 1997.

[51] Int. Cl.[7] .................................................. G01N 21/47
[52] U.S. Cl. ............................................................. 356/445
[58] Field of Search ...................................... 356/445–448

[56] References Cited

U.S. PATENT DOCUMENTS

| | | | |
|---|---|---|---|
| 3,802,780 | 4/1974 | Helm et al. ............................... | 356/152 |
| 4,097,751 | 6/1978 | Egan et al. ............................... | 250/571 |
| 4,171,910 | 10/1979 | Derderian et al. ....................... | 356/124 |
| 4,368,982 | 1/1983 | Van Arnam et al. .................... | 356/445 |
| 4,373,819 | 2/1983 | Pallotta .................................... | 356/445 |
| 4,721,389 | 1/1988 | Dejaiffe .................................... | 356/445 |
| 5,233,186 | 8/1993 | Ringlien ............................... | 250/223 B |

*Primary Examiner*—Frank G. Font
*Assistant Examiner*—Michael P. Stafira
*Attorney, Agent, or Firm*—Thomas, Kayden, Horstemeyer & Risley, L.L.P.

[57] ABSTRACT

A system and method for measuring the retroreflectivity of materials. The system comprises a light source and a first optical pathway along which an illumination light beam travels originating from the light source and ending at a retroreflective surface to be measured. Also, a second optical pathway is provided along which a retroreflected beam travels back from the retroreflective surface to a sensor array. A processor is electrically coupled to the sensor array with an accompanying memory on which is stored operating logic adapted to determine the intensity of a predetermined pattern of the retroreflected beam incident to the sensor array which defines the retroreflected light which propagates from the retroreflective surface at a predetermined observation angle.

35 Claims, 8 Drawing Sheets

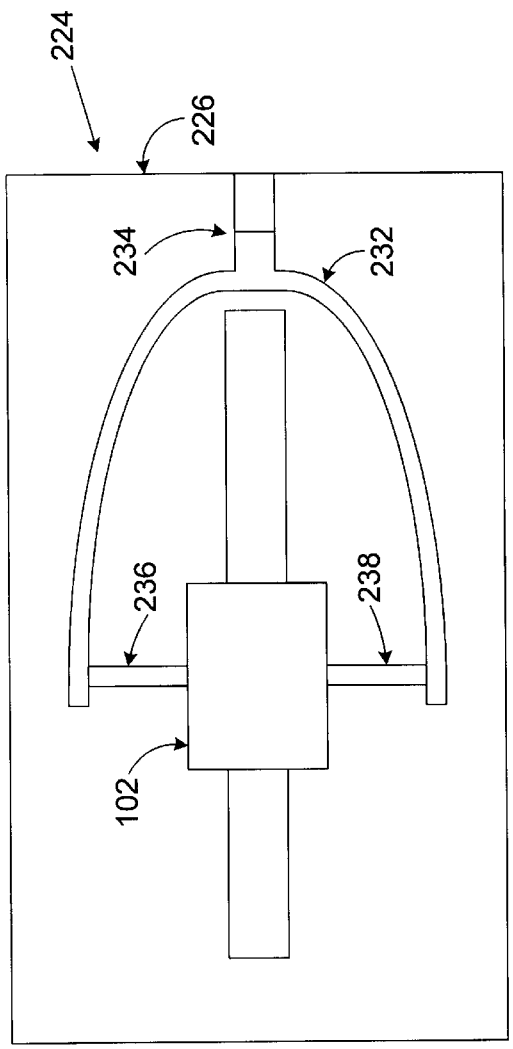
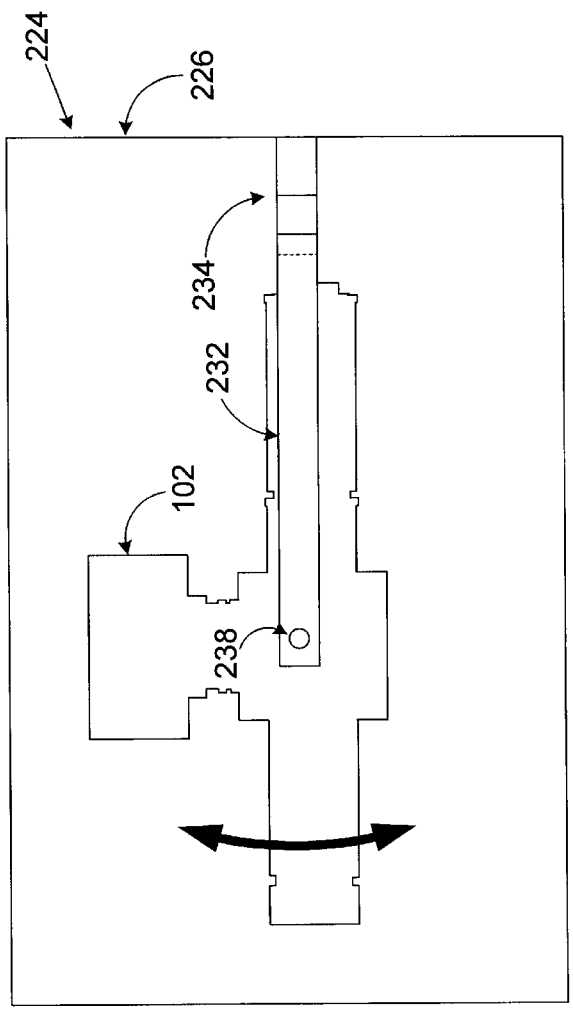
Fig. 8
Fig. 9

RETROREFLECTOMETER AND METHOD FOR MEASURING RETROREFLECTIVITY OF MATERIALS

CROSS REFERENCE TO RELATED APPLICATIONS

The present application claims priority to and the benefit of the filing date of Provisional Patent Application Ser. No. 60/044,740 filed Apr. 18, 1997, entitled "Retroreflectometer for Measuring the Characteristics of Retroreflective Highway Sign Material," which is incorporated herein by reference in its entirety.

FIELD OF THE INVENTION

The present invention relates to the field of retroreflection of light, and more particularly, to a system and method for measuring characteristics of retroreflective surfaces by using retroreflected light.

BACKGROUND OF THE INVENTION

Portable sign retroreflectometers quantify the reflective behavior of retroreflective materials used to make symbols and backgrounds on highway signs. As shown in FIG. 1, a retroreflectometer simulates illumination 51 from the headlights 53 of a motor vehicle 55 via an appropriate light source and measures the amount of retroreflected light 57 that propagates from the sign 59 in the direction of the driver's eyes is retroreflected directly back toward the headlights 53, but since the angular distribution of the reflected light has some angular spread, some of the light is directed toward the drivers eyes.

Current American Society for Testing and Materials (ASTM) standards specify that the sign 59 be illuminated by light situated at an illumination angle A1 of four degrees, and that the retroreflected light be measured at an observation angle A2 of 0.2 degrees above the retroreflected lobe which is directed back toward the headlights 53. Retroreflectometers which follow this standard simulate the angular separation between the headlights and a driver's eyes for a sign 150 to 200 meters in the distance. European standards require an illumination angle A1 of five degrees and an observation angle of 0.33 degrees.

In order to accomplish the above simulation, typical prior art retroreflectometers employ a single-element photodetector positioned relative to an illumination lamp such that the photodetector receives the retroreflected light at the observation angle. However, these devices have drawbacks. First, where the single-element detector is positioned behind or near the light source, it can be difficult to eliminate the light interference from the light source. Also, the angles of reflection should be very precise to ensure accurate measuring. This accuracy necessitates a bulky rigid structure to ensure a proper angle, etc.

In some cases, a beam splitter is used to separate the retroreflected light from the illumination light. The single-element detector is positioned to allow the retroreflected light to fall upon it. The retroreflected light incident to the single-element detector is typically round in shape, with the intensity being Gaussian in nature, with more intense light at the center and less intensity at the edges. In order to determine the intensity at the edges, prior art devices define an annulus which is centered at the center of the incident retroreflected light. The annulus is typically defined by placing a precise mask over the single-element detector that only allows the retroreflected light to pass through what falls in the annulus region which is defined by the observation angle as discussed previously. However, this configuration is not without its drawbacks.

Specifically, the angle of the splitter is precisely placed to ensure that the retroreflected light strikes the mask centered on the annulus. For example, if the single-element detector is separated from the beam splitter by 10 mm and the detector is 175 microns in diameter, then the angular position of the beam splitter is necessarily held to less than one milliradian and the detector positioned to within a tolerance of 17.5 microns in order that the required observation angle A2 of 0.2° be maintained to within 20%. Such precision necessitates bulky structure to ensure that the splitter does not move, even though the unit is handled roughly. Note that the mask which define the annulus is employed in some prior art devices without a splitter. These devices also necessitate bulky and precise structure to ensure that component parts maintain precise positions for accurate readings. Thus, the cost of manufacturing retroreflectometers according to the prior art is undesirably high due to the need for precision component parts and assembly. Also, these devices lack flexibility due to the nature of the single element detector.

In light of the forgoing, there is a need for a retroreflectometer which can accurately measure the intensity of retroreflected light within a predetermined area without the need for expensive and bulky structure, providing maximum flexibility in the nature of the predetermined area.

SUMMARY OF THE INVENTION

The present invention provides for a system and method for measuring the retroreflectivity of materials. The system comprises a light source and a first optical pathway along which an illumination light beam travels originating from the light source and ending at a retroreflective surface to be measured. Also, a second optical pathway is provided along which a retroreflected beam travels back from the retroreflective surface to a sensor array. A processor is electrically coupled to the sensor array with an accompanying memory on which is stored operating logic adapted to determine the intensity of a predetermined pattern of the retroreflected beam incident to the sensor array which defines the retroreflected light which propagates from the retroreflective surface at a predetermined observation angle.

The method of measuring the retroreflectivity of materials according to the present invention includes the steps of generating a light beam from a light source, directing the light beam from the light source to a retroreflective surface, and directing a retroreflected beam from the retroreflective surface to a sensor array. Finally, the intensity of the distribution of retroreflected light beam incident to the sensor array is determined.

Other features and advantages of the present invention will become apparent to one with skill in the art upon examination of the following drawings and detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 8 is a drawing showing the top view of an alignment fixture designed to hold the retroreflectometer of FIG. 2; and FIG. 9 is a drawing showing the top view of an alignment fixture designed to hold the retroreflectometer of FIG. 2.

DETAILED DESCRIPTION OF THE PREFERRED EMBODIMENT

Figure 2:
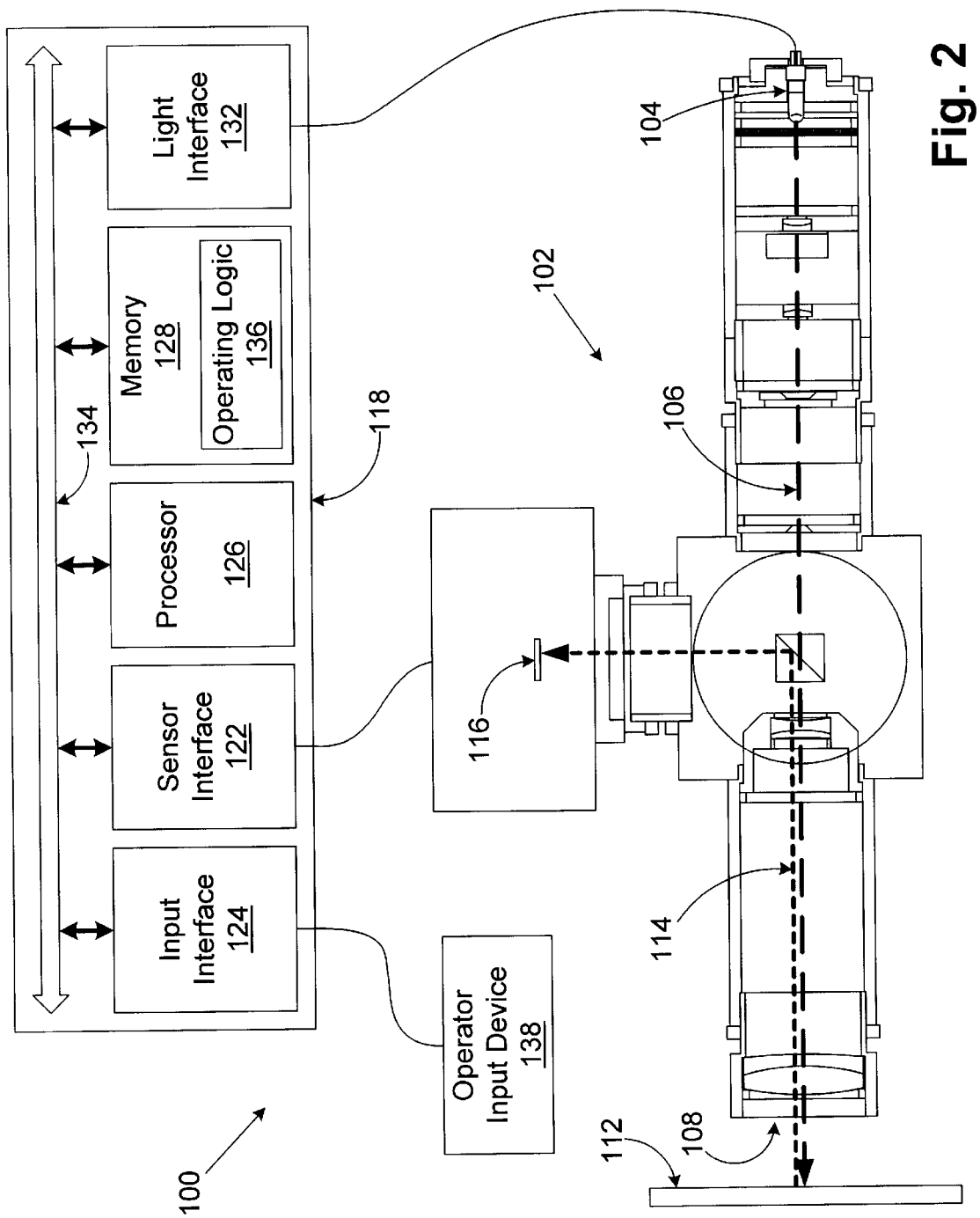
FIG. 2 is a drawing showing the system for measuring the retroreflectivity of materials according to the preferred embodiment of the present invention.

Turning to FIG. 2, shown is the system 100 for measuring the retroreflectivity of materials. The system 100 features a retroreflectometer 102 with a light source 104 at one end. The light source generates light that propagates along a first optical pathway 106 and exits the retroreflectometer 102 at an exit face 108 falling upon a sample surface 112, the retroreflectivity of which is to be measured. Retroreflected light then leaves the sample surface 112 and follows a second optical pathway 114 falling upon a sensor array 116.

The sensor array 116 is electrically coupled to a computer control system 118 through a sensor interface 122. The computer control system also features an operator input interface 124, a processor 126, a memory 128, and a light interface 132. The operator input interface 124, sensor interface 122, memory 128, and light interface 132 are in electrical communication with the processor 126 via the local interface 134, for example, one or more buses. The computer control system 118 operates pursuant to the operating logic 136 stored in the memory 128 and executed by the processor 126. An operator input device 138 is electrically connected to the input interface 124 to provide for operator control of the system.

To describe the general operation of the above system 100, first, the retroreflectometer 102 is aimed at the retroreflective surface 112 to be measured. The processor 126, operating according to the operating logic 136, will cause the light source 104 to turn on, sending an illuminating light beam along the first optical pathway 106 to the sample surface 112. Retroreflected light from the sample surface 112 then propagates along the second optical pathway 114, striking the sensor array 116. The information regarding the intensity of the incident retroreflected light beam is communicated from the sensor array 116 to the computer system 118. The processor 126 then calculates the desired intensity of the retroreflected light beam at the observation angle A2 (FIG. 1) pursuant to the operating logic 136 stored in memory 128.

It should be understood that in other embodiments, the computer control system 118 may actually be a specially designed logical circuit that does not employ a processor as shown in the preferred embodiment described herein.

Figure 3:
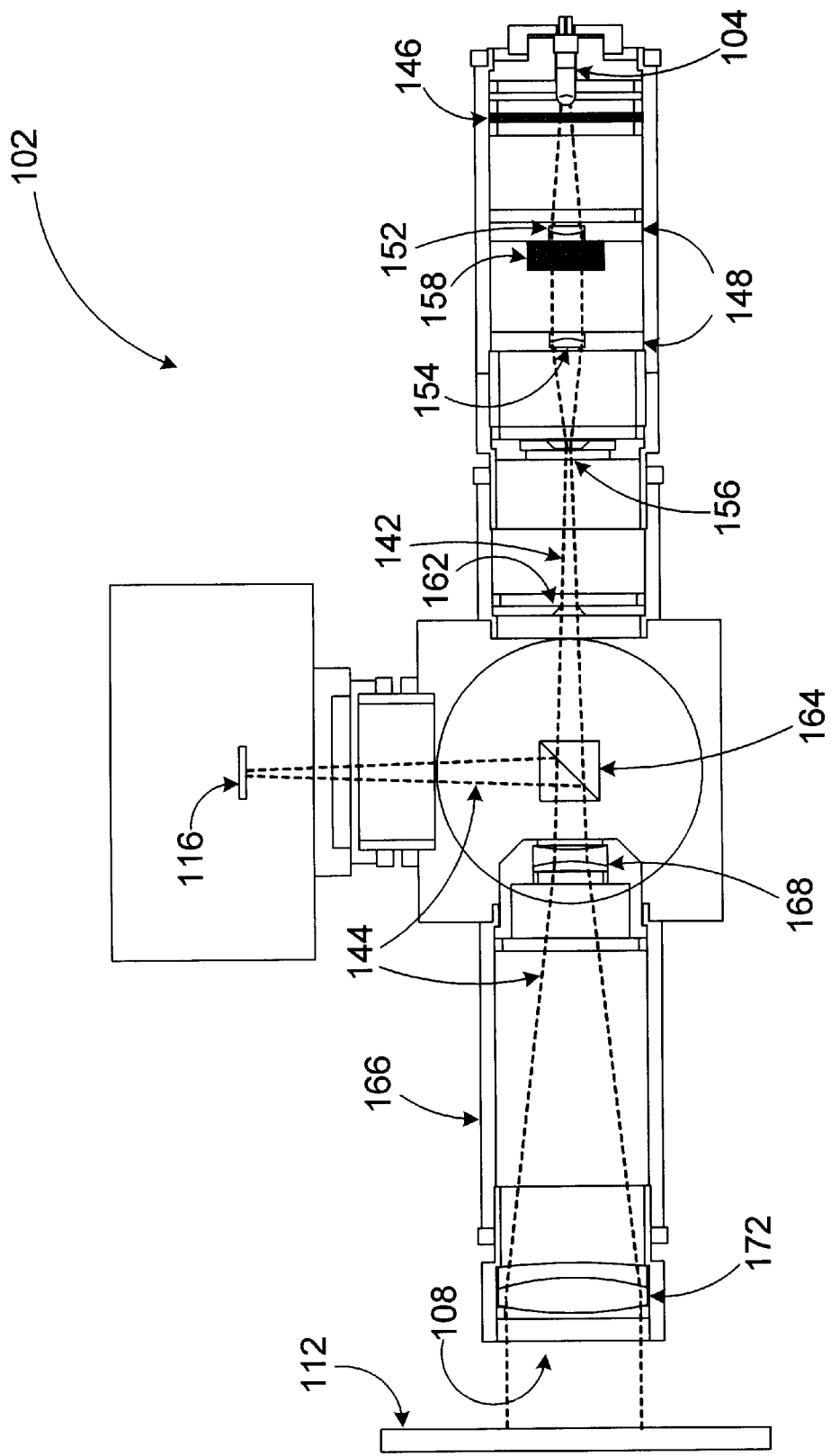
FIG. 3 is a drawing showing the light beam and the retroreflected beam of the system of FIG. 2.

Referring next to FIG. 3, shown is the retroreflectometer 102 of FIG. 2. According to the present invention, an illumination light beam 142 originates at the light source 104 and propagates along a first optical pathway 106 (FIG. 2) and strikes the sample surface 112. A retroreflective beam 144 then emanates from the sample surface 112 and propagates along the second optical pathway 114 (FIG. 2) to the sensor array 116.

Disposed along the first and second optical pathways 106 and 114 are various elements which optically process and filter the illumination light beam 142 and the retroreflected beam 144. Specifically, the light source 104 comprises a light bulb chosen to match the spectral distribution of the light source being simulated (i.e. in the preferred embodiment of the present invention, the simulated light source would be the headlights 53 (FIG. 1) of a motor vehicle 55 (FIG. 1)).

The illumination light beam 142 propagates from the light source 104 through a diffuser 146. The diffuser 146 ensures that the light from the light source 104 is scattered, thereby preventing any patterns of light in the illumination light beam 142 created by the light source 104. Next, the illumination light beam 142 is processed by a condenser 148 which has a first lens 152 and a second lens 154. The condenser 148 serves to focus the light on a pinhole aperture 156.

Disposed in the condenser 148 is a spectral filter 158. The spectral filter 158 features a spectral response that is similar to that of the human eye and is important because it allows the sensor array 116 to simulate the response of a human eye. To explain further, the human eye is most sensitive around the green spectrum and cannot see infrared wavelengths. Since the human eye cannot see infrared wavelengths, then neither should the sensor array 116 which simulates the human eye. The spectral filter 158 ensures that the sensor array 116 is not stimulated by light outside of the spectral response of the human eye for accurate simulation. This ensures that the light which ultimately strikes the sample 112 is similar to that seen by the driver of a motor vehicle due to the headlights 53 which would illuminate road signs.

The illumination light beam 142 then passes through the pinhole aperture 156 which features an angular size that results in an angular propagation of the illumination light beam 142 of 0.1 degrees or less, as seen from the exit face 108 which is specified in the ASTM standard for sign retroreflectometry. The illumination light beam 142 passes through a scraper aperture 162 in order to eliminate unwanted stray light. The illumination light beam 142 then passes through a splitter 164 and a telephoto-type lens 166 which is comprised of a diverging lens 168 and a focusing lens 172. The telephoto lens 166 collimates the light as it leaves the exit face 108 and strikes the sample surface 112.

The retroreflected beam 144 emanates from the sample surface 112 and retraces the path of the illumination light beam 142 back through the telephoto lens 166 and strikes the splitter 164. The retroreflective beam 144 is reflected by the splitter 164 toward the direction of the sensor array 116. The splitter 164 is oriented so that the retroreflective beam 144 will strike the sensing surface of the sensor array 116.

Note that although the spectral filter 158 is located in the condenser 148, it is possible that the spectral filter be placed anywhere within the first and second optical pathways 106 (FIG. 2) and 114 (FIG. 2), whichever is most convenient and economical. The primary concern is that the retroreflected light which falls onto the sensor array 116 be filtered by the spectral filter 158. Whether this is accomplished by filtering the illumination beam 142 or the retroreflected light beam 144 is of little consequence.

Figure 4:
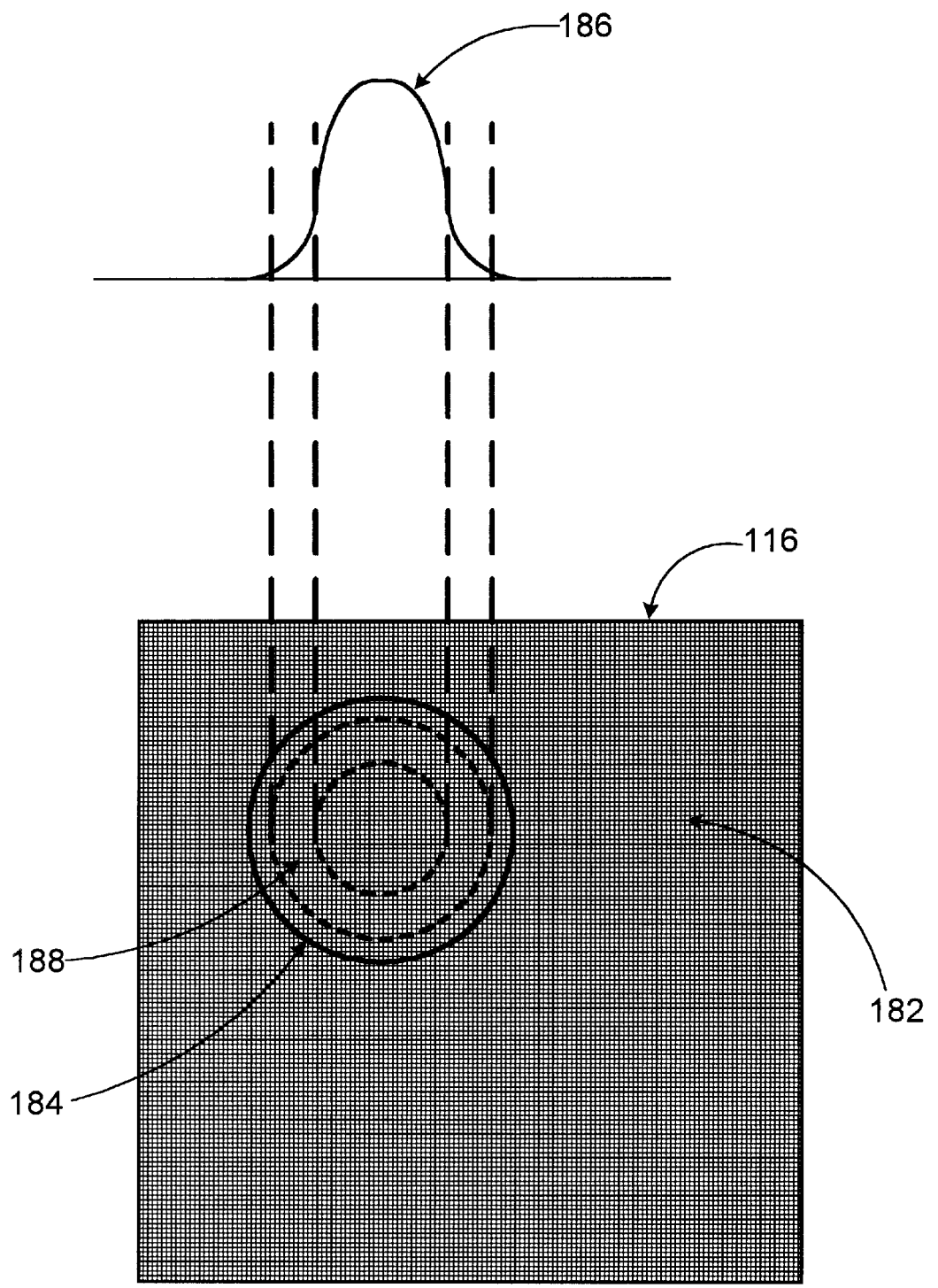
FIG. 4 is a drawing showing the incident light on the sensor of FIG. 2.

Turning to FIG. 4, shown is the sensing surface area of the sensor array 116. The sensor array 116 may be comprised of hundreds and even thousands of small pixel sensors 182, each pixel sensor 182 sensing the intensity of light incident to it. For example, an acceptable sensor array 116 may feature a resolution of 753×244 pixel sensors 182 for a total of 183,732 pixel sensors 182, however, it should be understood that a greater or lesser resolution may suffice with a corresponding greater or lesser number of pixel sensors 182. The specific dimensions of the pixel sensors 182 may be, for example, 11.5×27 microns in size. An incident retroreflected light pattern 184 is shown on the sensor array 116. Generally, the pattern of the retroreflected light beam 144 (FIG. 3) is circular in nature. The retroreflected beam intensity 186 is generally Gaussian in nature, with greater intensity in the middle of the circle and less intensity at the edges as shown.

In order to determine the intensity of the retroreflected light 144 (FIG. 3) at the observation angle A2 (FIG. 1) according to the ASTM standard, an annulus 188 is defined on the sensor array 116 that is centered on the incident retroreflected light pattern 184. The overall size of the annulus 188 dictated by the precise inner and outer diameters depends upon the precise observation angle A2 that the retroreflectometer 102 simulates, as well as the effective focal length of the telephoto lens 166. For example, shorter focal lengths produce smaller annuluses 188 and a longer focal lengths produce larger annuluses 188. Note, however, that although the annulus 188 is defined on the sensor array 116 according to the preferred embodiment of the present invention, the flexibility of the sensor array 116 allows any geometrical shape in the retroreflected pattern 184 to be defined by the operating logic 136.

The sensor array 116 can be of the type which is used in inexpensive black and white television cameras, such as a charge coupled device (CCD) detector array. Note that the pixel sensors 182 are precisely located in the sensor array 116, and the sensor array 116 is comparatively large, typically measuring 6.6 mm by 4.4 mm. Also the size of the retroreflected light pattern 184 is the same size as the pinhole aperture 156 (FIG. 3), the sensor array 116 being placed equidistant from the splitter 164 as the pinhole aperture 156. Note that a digital camera or a frame grabber can be used to perform the functions of the sensor array 116.

Figure 5:
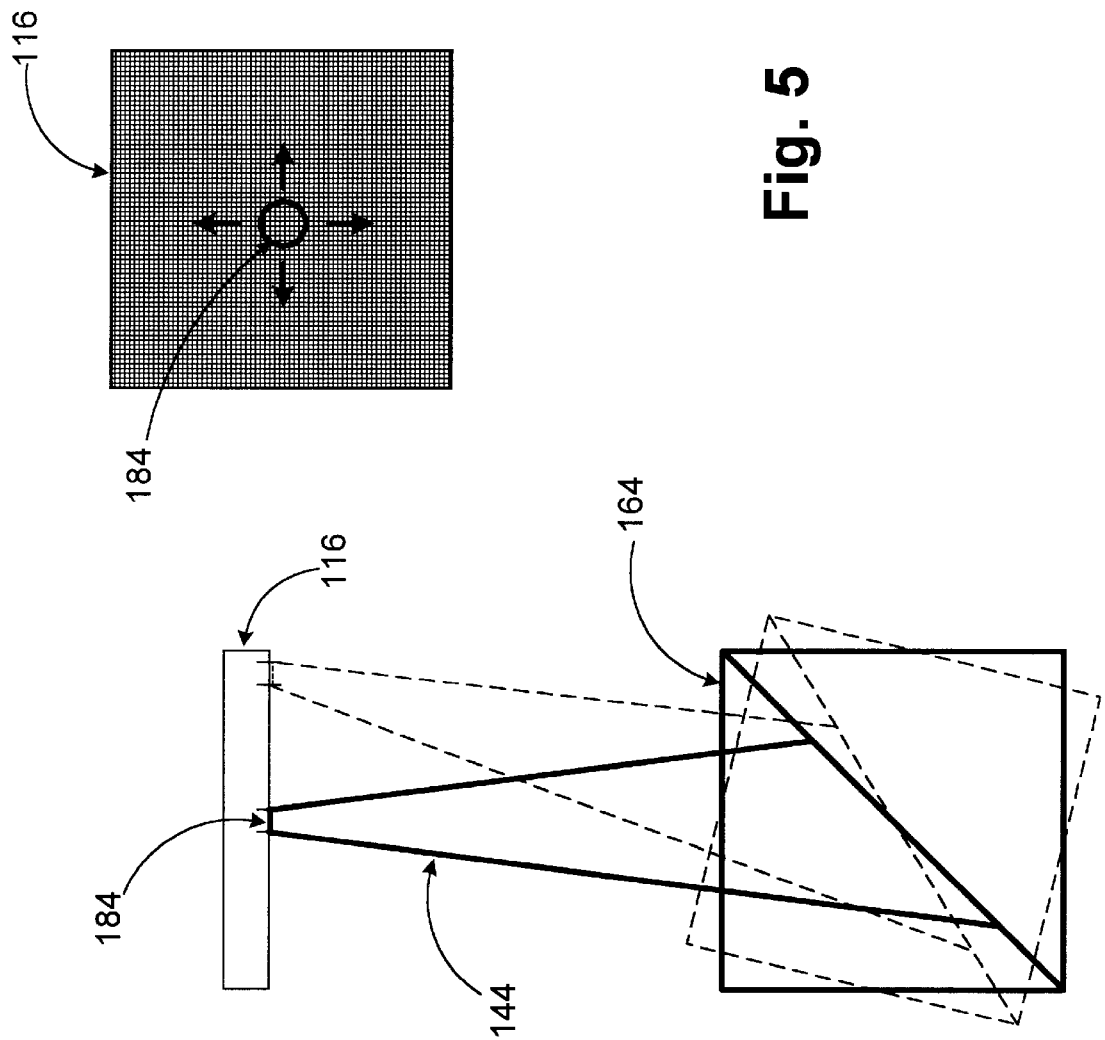
FIG. 5 is a drawing showing the positioning tolerance of the incident retroreflected light on the sensor array of FIG. 2.

Turning to FIG. 5, shown is the beam splitter 164 as it reflects the retroreflected beam 144 onto the sensor array 116. The use of the sensor array 116 provides a distinct advantage in that the splitter 164 need not be oriented with great precision so as to locate the incident retroreflected light pattern 184 at a particular point on the sensor array 116. The sensor array 116 allows for a certain amount of rotation and disorientation of the splitter 164 while still capturing the incident retroreflected light pattern 184 as shown. In fact, the incident retroreflected light pattern 184 may be located at any point within the sensing surface of the sensing array 116. Thus, the sensor array 116 defines a retroreflected light pattern positioning tolerance which is the range of allowable movement of the incident retroreflected light pattern 184, due to the area of the sensor array 116 that exceeds the area of the incident retroreflected light pattern 184. Because of this tolerance, the beam splitter 164 may be held by less bulky structure since the positioning tolerance is much greater than prior art retroreflectometers. Also, the operation in which the beam splitter 164 is aligned during assembly is much less precise and time consuming in addition to the fact that component parts need not be fabricated to tight dimensional tolerances because of the larger positioning tolerance of the present invention. Consequently, the cost of production of such a device falls due to the less precise and rigid nature of the retroreflectometer 102.

Figure 6:
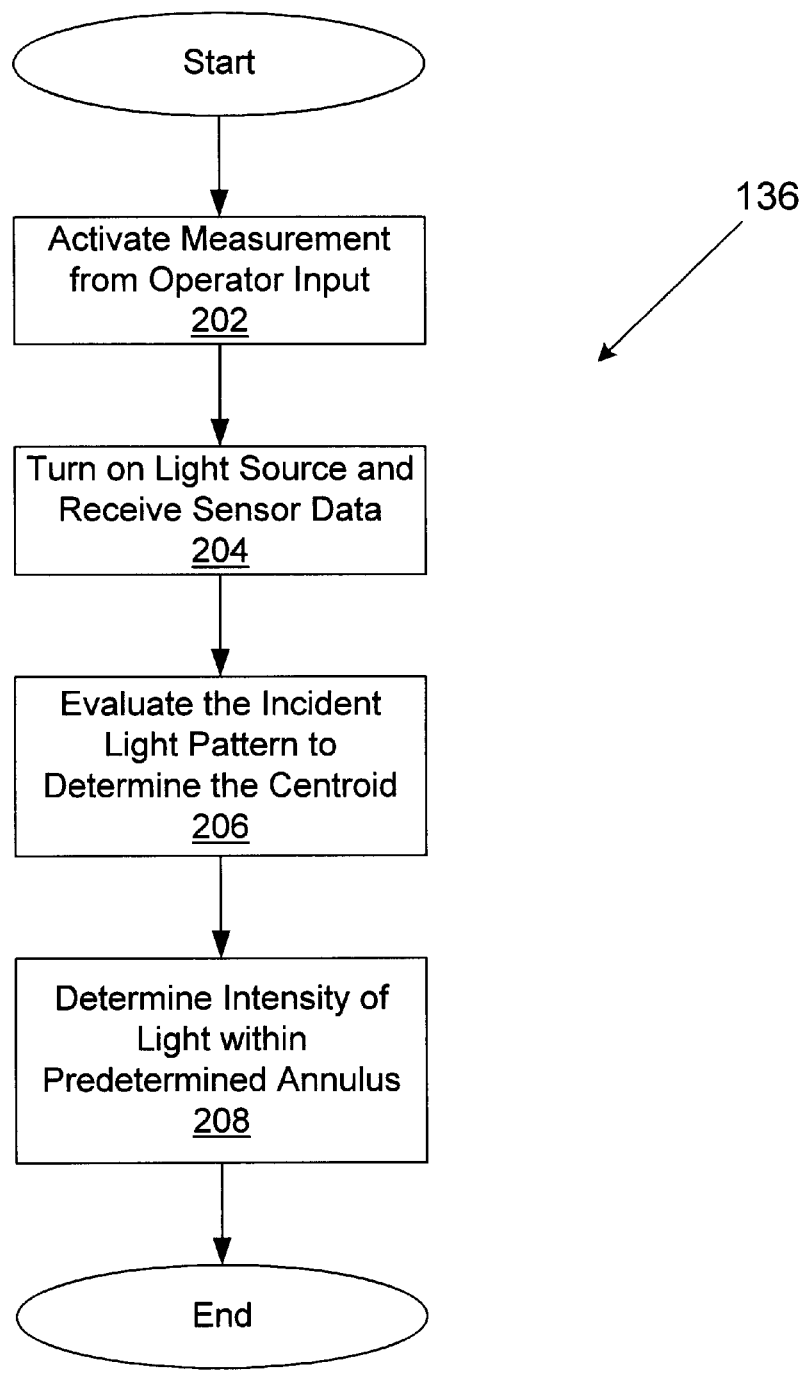
FIG. 6 is a flow diagram showing the operating logic of the system of FIG. 2.

With reference to FIG. 6, shown is the operating logic 136 (FIG. 2) which guides the operation of the system 100 (FIG. 2). In block 202, the operator input device 138 (FIG. 2) is manipulated to activate the measurement of a retroreflective sample surface 112 (FIG. 2). The operator input device 138 may comprise a push button, keyboard, switch, touch pad, touch screen, mouse, or other similar input device. Once the measurement cycle has begun, as indicated in block 204, the processor 126 causes the light source 104 to illuminate via the light interface 132. The light interface 132 may have a discrete voltage or current output to accomplish this task. Also, the light may be turned on manually. The retroreflected light beam 144 is then received by the sensor array 116 (FIG. 2) and corresponding data originating at sensor array 116 is sent to the processor 126 via the sensor interface 122.

Next, in block 206, the incident retroreflected light pattern 184 (FIG. 4) is examined to determine its center or centroid. This may be accomplished by choosing a random point on the sensor array 116, multiplying the intensity of the incident light onto each pixel sensor 182 (FIG. 4) times the distance between the chosen pixel sensor 182 and the randomly chosen point, and calculating the average of all the multiplications performed to obtain a centroid location relative to the randomly chosen point. This is done in both the X and Y directions.

The center of the incident retroreflected light pattern 184 may also be found by first defining a patch of pixel sensors 182 on which the portion of the retroreflected light beam 144 with the greatest intensity falls. As stated previously, the intensity of the retroreflected light beam 144 is Gaussian in nature with the greatest intensity in the center (see FIG. 4). Thus, the center of the incident retroreflected light pattern 184 comprises retroreflected light of the greatest intensity. Accordingly, a predetermined threshold of retroreflected light intensity that falls upon the pixel sensors 182 is first defined. Only those pixel sensors 182 which sense an intensity of retroreflected light above the predefined threshold are included in the patch. The centroid of the patch is then calculated in the same manner as the calculation of the centroid of the entire incident retroreflected light pattern 184 discussed previously. The calculation of the centroid of the patch is advantageous as there are less calculations to perform and, consequently, the determination of the centroid of the incident retroreflected light pattern 184 takes less time.

In yet another approach for determining the center of the incident retroreflected light pattern 184, the sensor pixel 182 upon which the greatest intensity of retroreflected light falls is first identified. Next a patch of predetermined size centered around this sensor pixel 182. The centroid of this patch is then calculated in the same manner described above. This approach would allow the determination of the center of an incident retroreflected light pattern 184 that is larger than the sensing surface area of the sensor array 116. However, the ultimate annulus 188 or other predefined shape or portion of the retroreflected light beam 144 should fall completely within the sensing surface area of the sensor array 116 in order to determine the intensity of the retroreflected light beam 144 at the observation angle A2.

Figure 1:
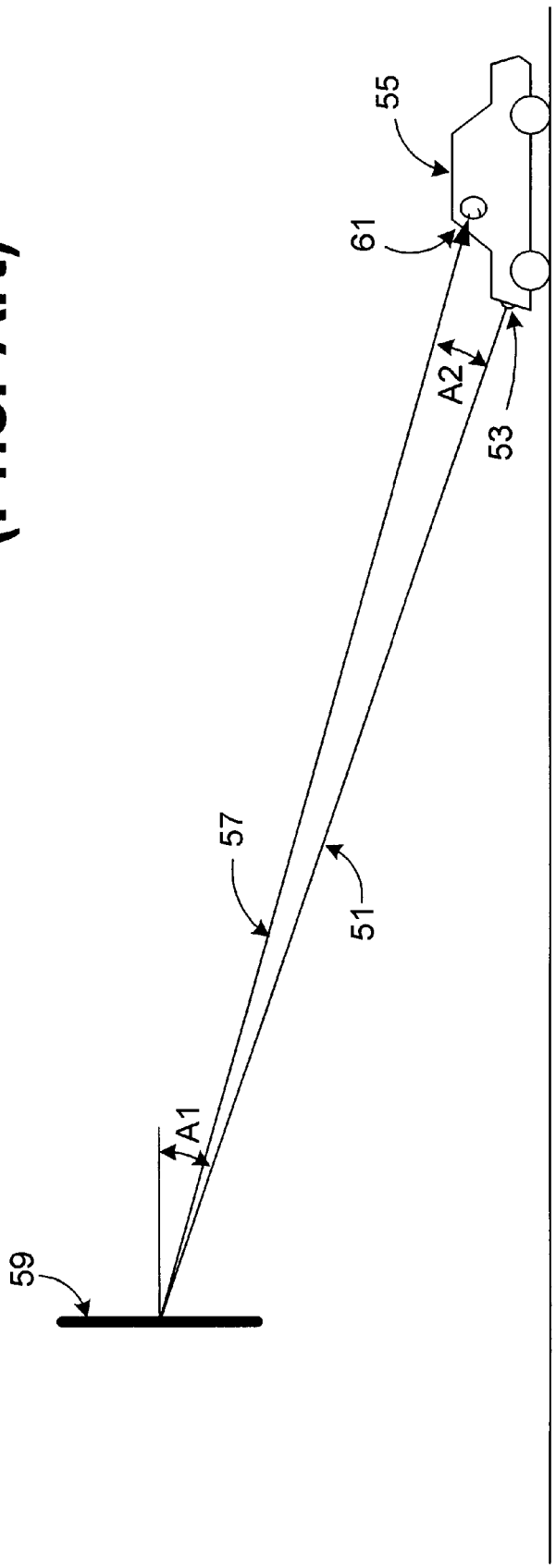
FIG. 1 is a drawing showing the illumination and observation angles of retroreflected light.

In accordance with block 208, the portion of the retroreflected light 144 (FIG. 3) which falls within the predetermined annulus 188 is determined. The annulus 188 defines the portion of the retroreflected light 144 which propagates from the retroreflective sample surface 112 at the observation angle A2 (FIG. 1). This is accomplished by adding the sensing information of the pixel sensors 128 which lie within the predetermined annulus 188.

Figure 7:
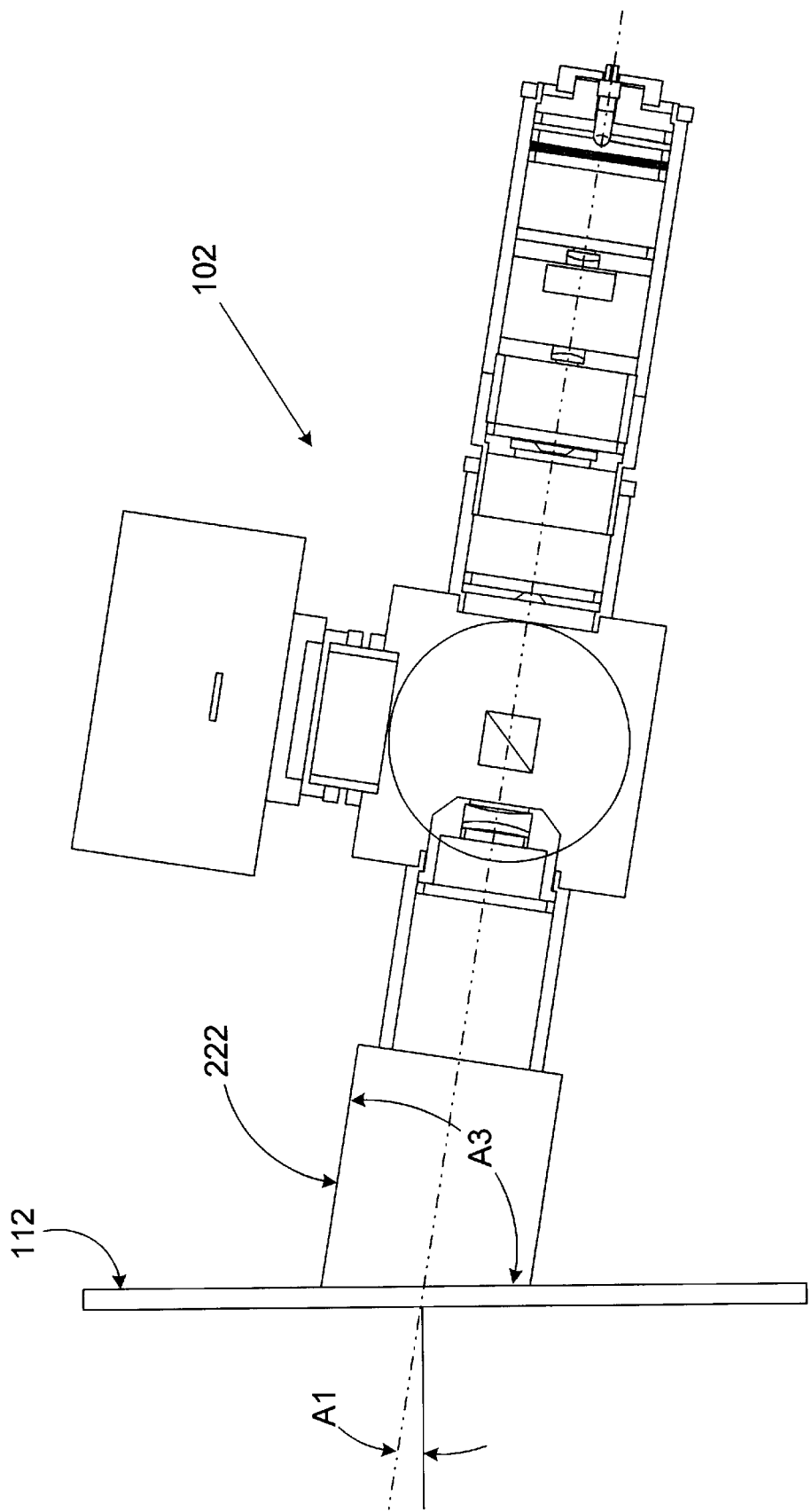
FIG. 7 is a drawing showing an alignment sleeve attached to the retroreflectometer of FIG. 2.

Turning next to FIG. 7, shown is the retroreflectometer 102 with the addition of an alignment sleeve 222 which is fixed over the end of retroreflectometer 102 on the side of the exit face 108 (FIG. 2). The end of the alignment sleeve 222 is cut at an angle A3 and mates with the sample surface 112 thereby creating the desired illumination angle A1.

With reference to FIGS. 8 and 9, shown is a top and side view of the retroreflectometer 102 placed within an alignment fixture 224. The alignment fixture 224 comprises an enclosure 226 with an open face 228. The enclosure 226 is shown to be box shaped, but may also be cylindrical or other shape. Within the enclosure 226 is wishbone member 232 which is rotatably attached to a pivot joint 234. The free ends of the wishbone member 232 are further attached to first and second pivot members 236 and 238. The retroreflectometer 102 can be rotated in a first dimension about the first and second pivot members 236 and 238 and a second dimension about the pivot joint 234. During use, the open face 228 of the alignment fixture 224 is placed against a sample surface (not shown) and the retroreflectivity is measured. The alignment fixture 224 may be affixed to the end of a pole which would enable the measurement of the retroreflectivity of road signs that are out of reach of a standing individual.

Many variations and modifications may be made to the preferred embodiment of the invention without departing substantially from the spirit and principles of the invention. All such modifications and variations are intended to be included herein within the scope of the present invention, as defined by the following claims.

What is claimed is:

1. A system for measuring retroreflectivity of materials, comprising:
   a light source;
   a sensor array;
   a first optical pathway to direct an illumination beam from the light source to a retroreflective surface;
   a second optical pathway to direct a retroreflected beam from the retroreflective surface to the sensor array;
   a local interface electrically coupled to the sensor array;
   a processor electrically coupled to the local interface;
   a memory electrically coupled to the local interface; and
   operating logic stored in the memory and executable by a processor to determine an intensity distribution of the retroreflected beam incident to the sensor array.

2. The system of claim 1, wherein an area of the retroreflected beam incident to the sensor array is smaller than a sensing surface area of the sensor array, thereby defining an incident retroreflected beam positioning tolerance.

3. The system of claim 1, wherein a predetermined portion of the retroreflected beam incident to the sensor array is smaller than a sensing surface area of the sensor array, thereby defining an incident retroreflected beam positioning tolerance.

4. The system of claim 1, wherein the operating logic further comprises logic to determine an intensity of a portion of the retroreflected beam incident to the sensor array that defines a predetermined angular separation between the illumination beam and the retroreflected beam.

5. The system of claim 3, wherein the operating logic further comprises logic to determine an intensity of the predetermined portion of the retroreflected beam incident to the sensor array that defines a predetermined angular separation between the illumination beam and the retroreflected beam.

6. The system of claim 4, wherein the logic to determine the intensity of the portion of the retroreflected beam incident to the sensor array that defines the predetermined angular separation further includes logic to determine a centroid of the retroreflected beam incident to the sensor array.

7. The system of claim 6, wherein the portion of the retroreflected beam incident to the sensor array is an annulus centered around the centroid.

8. A system for measuring the retroreflectivity of materials, comprising:
   a light source;
   a sensor array;
   a first optical pathway to direct an illumination beam from the light source to a retroreflective surface;
   a second optical pathway to direct a retroreflected beam from the retroreflective surface to the sensor array; and
   a logical circuit electrically coupled to the sensor array, the logic circuit configured to determine an intensity distribution of the retroreflected beam incident to the sensor array.

9. The system of claim 8, wherein an area of the retroreflected beam incident to the sensor array is smaller than a sensing surface area of the sensor array, thereby defining an incident retroreflected beam positioning tolerance.

10. The system of claim 8, wherein a predetermined portion of the retroreflected beam incident to the sensor array is smaller than a sensing surface area of the sensor array, thereby defining an incident retroreflected beam positioning tolerance.

11. The system of claim 8, wherein the logical circuit further comprises logical circuitry to determine the intensity of a portion of the retroreflected beam incident to the sensor array that defines a predetermined angular separation between the illumination beam and the retroreflected beam.

12. The system of claim 10, wherein the logical circuit further comprises logical circuitry configured to determine the intensity of a predetermined portion of the retroreflected beam incident to the sensor array that defines a predetermined angular separation between the illumination beam and the retroreflected beam.

13. The system of claim 11, wherein the logical circuit is further configured to determine a centroid of the retroreflected beam incident to the sensor array.

14. The system of claim 13, wherein the portion of the incident retroreflected beam is an annulus centered around the centroid.

15. A system for measuring the retroreflectivity of materials, comprising:
   a light source;
   a sensor array;
   means for directing an illumination beam from the light source to a retroreflective surface;
   means for directing a retroreflected beam from the retroreflective surface to the sensor array; and
   means for determining an intensity distribution of the retroreflected beam incident to the sensor array.

16. The system of claim 15, wherein an area of the retroreflected beam incident to the sensor array is smaller than a sensing surface area of the sensor array, thereby defining an incident retroreflected beam positioning tolerance.

17. The system of claim 15, wherein a predetermined portion of the retroreflected beam incident to the sensor array is smaller than a sensing surface area of the sensor array, thereby dining an incident retroreflected beam positioning tolerance.

18. The system of claim 15, wherein the means for determining the intensity distribution of the retroreflected beam incident to the sensor array further comprises means for determining the intensity of a portion of the retroreflected beam incident to the sensor array that defines a predetermined angular separation between the illumination beam and the retroreflected beam.

19. The system of claim 17, wherein the means for determining the intensity of the retroreflected beam incident to the sensor array further comprises means for determining the intensity of the predetermined portion of the retroreflected beam incident to the sensor array that defines a predetermined angular separation between the illumination beam and the retroreflected beam.

20. The system of claim 18, wherein the means for determining the intensity of the portion of the retroreflected beam incident to the sensor array that defines the predetermined angular separation further comprises means for determining a centroid of the retroreflected beam incident to the sensor array.

21. The system of claim 20, wherein the portion of the retroreflected beam incident to the sensor array is an annulus centered at the centroid.

22. A method for measuring the retroreflectivity of materials, comprising the steps of:
generating an illumination beam from a light source;
directing the illumination beam from the light source to a retroreflective surface;
directing a retroreflected beam from the retroreflective surface to a sensor array; and
determining an intensity distribution of the retroreflected beam incident to the sensor array.

23. The method of claim 22, further comprising the step of positioning the retroreflected beam incident to the sensor array within a surface area of the sensor array.

24. The method of claim 22, wherein the step of determining the intensity distribution of the retroreflected beam incident to the sensor array further comprises the step of determining the intensity of a portion of the retroreflected beam incident to the sensor array that defines a predetermined angular separation between the illumination beam and the retroreflected beam.

25. The method of claim 24, wherein the step of determining the intensity of a portion of the retroreflected beam incident to the sensor array that defines the predetermined angular separation further comprises the step of determining a centroid of the retroreflected beam incident to the sensor array.

26. The method of claim 25, wherein the step of determining the intensity of a portion of the retroreflected beam incident to the sensor array that defines the predetermined angular separation further comprises the step of defining an annulus in the retroreflected beam incident to the sensor array centered at the centroid.

27. A system for generating an intensity distribution indicating an angular separation between an illumination beam and a retroreflected beam to determine a retroreflectivity of a sample surface, comprising:
a light source to generate the illumination beam;
a sensor array to receive a retroreflected beam;
a first optical pathway extending from the light source to an exit face to direct a propagation of the illumination beam through the exit face; and
a second optical pathway extending from the exit face to the sensor array to direct a propagation of the retroreflected beam received through the exit face, the sensor array generating the intensity distribution in response to the retroreflected beam incident to the sensor array.

28. The system of claim 27, wherein an area of the retroreflected beam incident to the sensor array is smaller than a sensing surface area of the sensor array, thereby defining an incident retroreflected beam positioning tolerance.

29. The system of claim 27, wherein a predetermined portion of the retroreflected beam incident to the sensor array is smaller than a sensing surface area of the sensor array, thereby defining an incident retroreflected beam positioning tolerance.

30. The system of claim 29, wherein the predetermined portion of the retroreflected beam incident to the sensor array is an annulus centered around the centroid.

31. A system for generating an intensity distribution indicating an angular separation between an illumination beam and a retroreflected beam to determine a retroreflectivity of a sample surface, comprising:
a light source to generate the illumination beam;
a sensor array to receive a retroreflected beam;
means for directing the illumination beam from the light source to an exit face; and
means for directing the retroreflected beam received through the exit face to the sensor array, the sensor array generating the intensity distribution in response to the retroreflected beam incident to the sensor array.

32. The system of claim 31, wherein an area of the retroreflected beam incident to the sensor array is smaller than a sensing surface area of the sensor array, thereby defining an incident retroreflected beam positioning tolerance.

33. The system of claim 31, wherein a predetermined portion of the retroreflected beam incident to the sensor array is smaller than a sensing surface area of the sensor array, thereby defining an incident retroreflected beam positioning tolerance.

34. The system of claim 33, wherein the predetermined portion of the retroreflected beam incident to the sensor array is an annulus centered around the centroid.

35. A method for generating an intensity distribution indicating an angular separation between an illumination beam and a retroreflected beam to determine a retroreflectivity of a sample surface, comprising the steps of:
generating the illumination beam using a light source;
directing the illumination beam from the light source to an exit face;
directing the retroreflected beam received through the exit face to a sensor array; and
generating the intensity distribution with the sensor array in response to the retroreflected beam incident to the sensor array.

* * * * *